United States Patent [19]

Butler

[11] 4,128,555

[45] Dec. 5, 1978

[54] 3-PHENOXYPYRIDINE MONOSULFATE AND A METHOD FOR ITS PRODUCTION

[75] Inventor: Donald E. Butler, Ann Arbor, Mich.

[73] Assignee: Warner-Lambert Company, Morris Plains, N.J.

[21] Appl. No.: 801,113

[22] Filed: May 27, 1977

Related U.S. Application Data

[63] Continuation-in-part of Ser. No. 751,933, Dec. 17, 1976, abandoned.

[51] Int. Cl.² .......................................... C07D 213/16
[52] U.S. Cl. .................................................. 546/290
[58] Field of Search ........................ 270/294.8 R, 297

[56] References Cited

U.S. PATENT DOCUMENTS

| | | | |
|---|---|---|---|
| 2,753,352 | 7/1956 | Bernstein et al. | 260/294.8 R |
| 3,429,689 | 2/1969 | Duerr et al. | 260/297 R |

OTHER PUBLICATIONS

Butler et al., J. Med. Chem., vol. 14(7), pp. 575–579, (1971).
Renshaw et al., J. Am. Chem. Soc., vol. 59(2), pp. 297–301 (Feb. 1937).

*Primary Examiner*—Alan L. Rotman
*Attorney, Agent, or Firm*—Stephen Raines; David B. Ehrlinger; Frank S. Chow

[57] ABSTRACT

3-Phenoxypyridine monosulfate, a pharmacological agent possessing mood elevating and cardiotonic properties. This compound is produced by reacting 3-phenoxypyridine with an equivalent amount of sulfuric acid.

1 Claim, No Drawings

3-PHENOXYPYRIDINE MONOSULFATE AND A METHOD FOR ITS PRODUCTION

This application is a continuation-in-part application of co-pending application Ser. No. 751,933, filed Dec. 17, 1976, now abandoned.

SUMMARY AND DETAILED DESCRIPTION

The present invention relates to 3-phenoxypyridine monosulfate which possesses cardiotonic and mood elevating properties and to a method for its preparation.

3-Phenoxypyridine is a compound which exhibits cardiotonic and mood elevating properties and has the following structure

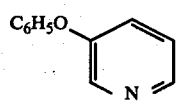

The preferred mode of administration of this drug is by the oral route in the form of a tablet or a capsule. Unfortunately, free amine bases are generally undesirable in oral formulations. In order to avoid having free amine bases in oral formulations, the corresponding acid-addition salts are employed, usually the hydrochloride. Unfortunately, 3-phenoxypyridine forms a very hygroscopic salt when reacted with hydrochloric acid. In addition, 3-phenoxypyridine does not appear in most instances to form an isolatable salt when coupled with the traditionally used carboxylic acids. The best organic salts prepared are the maleate and citraconate salts. However, the former possesses too low a melting point and the latter is economically undesirable. Certain instances where salt formation is possible, as in the cases of nitric acid and hydrobromic acid, problems are presented by the potential toxicity of the resulting acid-addition salt. Numerous acids were combined with 3-phenoxypyridine that normally form desirable crystalline products; however, in the present instance hygroscopic crystalline products could only be isolated or noncrystalline products resulted. Unexpectedly, one equivalent of 3-phenoxypyridine when reacted with one equivalent of sulfuric acid gives to an essentially nonhydroscopic, crystalline material, 3-phenoxypyridine monosulfate. This is exceptionally surprising since under normal laboratory conditions, using two equivalents of 3-phenoxypyridine and one equivalent of sulfuric acid, di(3-phenoxypyridine) sulfate, the more commonly prepared salt, cannot be isolated in a crystalline form. The monosulfate anion is relatively non-toxic and thus ideal for a pharmaceutical preparation.

The 3-phenoxypyridine monosulfate has been found to exist in two forms. A stable form which has a melting point of 107–109° C. and an unstable form having a melting point of 114.5° C. The unstable form is rarely isolated during the preparation of 3-phenoxypyridine monosulfate; however, when it is isolated it quickly reverts to the more stable form.

In accordance with the invention, 3-phenoxypyridine monosulfate can be produced by reacting 3-phenoxypyridine with sulfuric acid. One equivalent of 3-phenoxypyridine in a polar solvent, preferably a lower alkyl alcohol having from one to four carbon atoms, or a lower alkylnitrile wherein said alkyl group has from one to three carbon atoms, is treated with approximately an equivalent, preferably 0.9 to 1.1, amount of sulfuric acid (98 percent) on a molar basis. The quantity of solvent, the most preferred being 2-propanol or acetonitrile, which is employed may vary from about 0.5 ml. to about 5 ml. for each gm. of 3-phenoxypyridine present. The sulfuric acid is added at such a rate that the reaction temperature is maintained below 50° C. although the temperature is not critical. A crystalline product, 3-phenoxypyridine monosulfate, forms which is separated, preferably by filtration.

3-Phenoxypyridine monosulfate is administered for the purpose of inducing mood elevation in mammals, such as rodents, etc.

The compound of this invention, by elevating the mood of mammals suffering from mental depression is useful in treating all conditions wherein antidepressants are traditionally employed.

The effectiveness of the aforementioned compound is determined in the following manner.

A test entitled "Facilitation of Low Base Line Self-Stimulation Screen" which is based upon the procedure reported in "Life Sciences", 3 903 (1964), was used to determine the activity of the compound of this invention.

Adult male albino rats are implanted with permanent electrodes in the medial forebrain bundle of the posterior hypothalamus, an area of the brain which yields intense reward when stimulated. After the animals recover from surgery, they are trained in a Skinner box to press a lever to stimulate their own brains electrically, i.e., to self-stimulate.

After the animals become expert at self-stimulation, the stimulating current is reduced individually for each rat to a level moderately above the reward threshold, which causes self-stimulation rates to decrease correspondingly. Training sessions are run each day under these reduced current conditions until response rates stabilize. The slow response rates generated by these conditions serve as the behavioral base lines. One then proceeds to test whether various treatments increase self-stimulation rates above these base lines. During all tests the self-stimulation behavior of the animals is continuously recorded graphically on cumulative recorders. Drugs, when administered, are given preferably by the oral route.

A drug is considered "active" if the baseline rates of self-stimulation of the animals are clearly augmented by the agent. Such increases in self-stimulation are considered a strong indication that the drug has stimulated the adrenergic reward systems of the brain, and therefore the drug may act favorably upon mental depression.

3-Phenoxypyridine monosulfate exhibited an excitatory effect on self-stimulation at a dose level of from 5 mg./kg. to the maximum tested dose level of 80 mg./kg. The effect at 5 mg./kg. was weak, 10 mg./kg. was moderate, and 20, 40 and 80 mg./kg. was strong.

From variations of the above tests it was also observed that there are minimal signs of motor stimulation and no inhibition of monoamine oxidase.

In addition, the compounds of this invention may also be administered to mammals, such as dogs as a cardiotonic agent. More specifically, the compound of this invention may be used in the treatment of congestive heart failure, acute cardiogenic shock, myocardial ischemia and myocardial depression caused by barbiturates or other depressant agents.

The effectiveness of 3-phenoxypyridine monosulfate on cardiovascular function is shown in six adult mongrel dogs of either sex, weighing 12–20 kg. which are anesthetized. The animals are premedicated with morphine sulfate, 2 mg./kg. (intramuscular) and then anesthetized with sodium pentobarbital 35 mg./kg. (intravenous). Respiration is maintained using a respirator and blood gas and pH are monitored and maintained at normal values. Thoracotomy is performed through the 4th left intercoastal space for placement of an aortic electromagnetic flow probe at the origin of the aorta and Konigsberg pressure transducer in the left ventricle via the left atrium. The thorax is then closed and the femoral artery and vein cannulated for blood pressure measurement and drug injection, respectively. Electrodes are placed for lead II EKG.

To evaluate the effects of 3-phenoxypyridine monosulfate on cardiovascular function, the following primary signals are recorded: aortic blood flow, aortic blood pressure, left ventricular blood pressure, and electrocardiogram. Aortic blood flow is measured with an electromagnetic flow probe coupled to a blood flowmeter while aortic blood pressure is obtained using a pressure transducer. The transducer is located at phlebostatic level and the implanted catheter extended directly to the transducer. Transducer couplers are used for conditioning both pressure signals and electrocardiograms are recorded from the electrodes using an amplifier with a low frequency cut off of 0.05 Hz.

For assessment of cardiovascular performance, analog signals are recorded on a polygraph and simultaneously digitized and processed by a computer system. Electrocardiogram traces are visually scanned for possible drug effects. The primary cardiovascular parameters which are obtained include heart rate, systolic and diastolic aortic blood pressure, stroke volume, and peak aortic flow. Derived parameters are maximum left ventricular dp./dt., maximum first derivative of aortic flow, cardiac output, mean blood pressure, and calculated total peripheral resistance.

Prior to drug administration, an adequate control period is obtained. The 3-phenoxypyridine monosulfate is then injected (intravenous) through the femoral cannula. Animals are monitored for 45 minutes between each dose (the following doses are given, calculated as free base).

0.2 mg./kg. in 0.9% NaCl, 0.5 mg./ml. pH 7.4
0.4 mg./kg. (cumulative 0.6 mg./kg.), in 0.9% NaCl, 0.5 mg./ml., pH 7.4
1.4 mg./kg. (cumulative 2.0 mg./kg.), in 0.9% NaCl, 5.0 mg./ml., pH 3.6
4.0 mg./kg. (cumulative 6.0 mg./kg.), in 0.9% NaCl, 5.0 mg./ml., pH 3.6

Control studies are also done on three dogs, injecting the vehicle (0.9% NaCl) at the appropriate volume and pH, at the corresponding times.

It is found that the threshold dose of 3-phenoxypyridine monosulfate producing cardiovascular effects in the anesthetized dogs is 0.6 mg./kg. (cumulative) with pronounced effects seen at 2.0 and 6.0 mg./kg. (cumulative). The cardiovascular changes produced by the compound are slow in onset, achieving maximum effect by 45 minutes which plateaued for 2 hours after the last dose. 3-Phenoxypyridine monosulfate causes a marked positive inotropic effect as demonstrated by an increase in stroke volume (+38%), maximum 1st derivative of left ventricular pressure (+145%), peak aortic flow rate (+54%) and its 1st derivative (+107%). In addition, cardiac output increases 26% with little change in total peripheral resistance, resulting in a 30-35% increase in blood pressure, with systolic pressures often above 200 mm Hg. while heart rate is minimally affected. Control animals receiving only vehicle show no changes in cardiovascular performance during the course of the experiment.

The invention is illustrated by the following examples.

EXAMPLE 1

A solution of 523 g. of 3-phenoxypyridine in 750 ml. of 2-propanol is treated slowly with stirring with 303 g. of 98% sulfuric acid, while maintaining the temperature below 50° C. On cooling to room temperature, the mixture sets up solid. It is heated to 75° C., transferred to an acceptable container and allowed to cool to 50° C. and the crystalline product collected by filtration. The filtrate is allowed to stand at room temperature for 2 hours and the additional crystalline product is collected by filtration. The combined product is dried at reduced pressure to give 3-phenoxypyridine monosulfate, m.p. 103°–107° C. The salt is recrystallized from acetonitrile; after drying at reduced pressure it melts at 107°–109° C.

EXAMPLE 2

Acetonitrile (285 ml.) is cooled to 5° C. and with stirring and cooling and 95-98% sulfuric acid (18.3 ml.) is added in a dropwise manner with the temperature being maintained below 10° C. 3-Phenoxypyridine (57.0 g.) is added over fifteen minutes. When addition is complete the mixture is heated to 55° C. and the resulting solution is transferred to a convenient container and chilled in an ice bath. The crystalline product is collected by filtration and dried at 40° C. under house vacuum overnight, mp. 107°–109° if conducted at a rapid rate (3.5-5 on the Thomas-Hoover apparatus). If the melting point is carried out by very slowly raising the temperature of mp. of 114.5°–117° is obtained with what appears to be a phase change around 100°–110°.

What is claimed is:
1. 3-Phenoxypyridine monosulfate.
* * * * *